(12) United States Patent
Iketaki et al.

(10) Patent No.: US 6,576,117 B1
(45) Date of Patent: Jun. 10, 2003

(54) METHOD AND APPARATUS FOR ELECTROCHEMICAL MEASUREMENT USING STATISTICAL TECHNIQUE

(75) Inventors: Kazuo Iketaki, Kyoto (JP); Yoichi Inoue, Kyoto (JP); Katsumi Hamamoto, Kyoto (JP)

(73) Assignee: Arkray, Kyoto, Inc. (JP)

( * ) Notice: Subject to any disclaimer, the term of this patent is extended or adjusted under 35 U.S.C. 154(b) by 0 days.

(21) Appl. No.: 09/700,765

(22) PCT Filed: May 19, 1999

(86) PCT No.: PCT/JP99/02632

§ 371 (c)(1),
(2), (4) Date: Jan. 29, 2001

(87) PCT Pub. No.: WO99/60391

PCT Pub. Date: Nov. 25, 1999

(30) Foreign Application Priority Data

May 20, 1998 (JP) .............................................. 10-155213

(51) Int. Cl.$^7$ ............................................. G01N 27/327
(52) U.S. Cl. ............... 205/777.5; 204/400; 204/403.01; 204/403.11; 204/408
(58) Field of Search .................................... 204/400, 403, 204/408, 403.01, 403.11; 205/777.5; 702/99, 104

(56) References Cited

U.S. PATENT DOCUMENTS

| | | | |
|---|---|---|---|
| 4,775,456 A | 10/1988 | Shah et al. | |
| 5,243,516 A | 9/1993 | White | |
| 5,266,179 A | 11/1993 | Nankai et al. | |
| 5,469,369 A | * 11/1995 | Rose-Pehrsson et al. | ... 340/632 |
| 5,611,909 A | 3/1997 | Studer | |
| 5,723,284 A | 3/1998 | Ye | |
| 5,781,455 A | * 7/1998 | Hyodo | .................. 204/403 |

FOREIGN PATENT DOCUMENTS

| | | |
|---|---|---|
| EP | 0 679 720 | 11/1995 |
| EP | 0 741 186 | 11/1996 |
| EP | 0 878 713 | 11/1998 |
| JP | 60-211350 | 10/1985 |
| JP | 61-3048 | 9/1986 |
| JP | 62-64940 | 3/1987 |
| JP | 4-328459 | 11/1992 |
| JP | 4-357452 | 12/1992 |
| JP | 8-503304 | 4/1996 |
| JP | 8-304340 | 11/1996 |
| JP | 2651278 | 5/1997 |
| JP | 9-201337 | 8/1997 |
| JP | 10-10130 | 1/1998 |
| JP | 10-318963 | 12/1998 |
| WO | WO 94/29704 | 12/1994 |

\* cited by examiner

*Primary Examiner*—Robert J. Warden, Sr.
*Assistant Examiner*—Kaj K. Olsen
(74) *Attorney, Agent, or Firm*—Merchant & Gould P.C.

(57) ABSTRACT

A predetermined voltage is applied to a biosensor twice to promote an electrochemical reaction, and the following parameters (P1 and P2) are calculated from the values of detected current. A statistical technique is used with these parameters to compensate for errors so that the concentration of an object can be determined. P1: the ratio (If/Ib) of the maximum current (If) or a current occurring the maximum in the first excitation to a current (Ib) read at any point in the second excitation. P2: a current (Ib) read at any point in the second excitation.

10 Claims, 3 Drawing Sheets

METHOD AND APPARATUS FOR ELECTROCHEMICAL MEASUREMENT USING STATISTICAL TECHNIQUE

TECHNICAL FIELD

This invention relates to a method for electrochemically measuring a concentration of an analyte in a sample. More specifically, this invention relates to a method for electrochemical measurement to obtain a concentration of analyte in a sample by correcting errors caused by sample physical properties and sensor sensitivity.

BACKGROUND ART

Recently in the fields of biochemistry, clinical medicine or the like, electrochemical measurement has been used to measure a concentration of an analyte in a sample in a rapid and simple manner. An electrochemical measurement is a method to measure an analyte in a sample by using an electric signal such as a current that is obtained from a chemical reaction or an enzymatic reaction.

For example, the concentration of glucose in a blood is measured in the following process. Glucose as an analyte in a blood sample reacts with glucoseoxidase (GOD) to generate a GOD·H2 complex, from which electrons are liberated by an electron carrier such as potassium ferricyanide. The free electrons are captured in an electrode to calculate a current value, and thus, a glucose concentration is obtained by calculation from a calibration curve, a calibration formula or the like that is produced previously.

In an electrochemical measurement, a disposable device called a biosensor is commonly used. A biosensor has a reaction layer and an electrode system.

A reaction layer comprises a reaction reagent, an enzyme or a matrix to react specifically with an analyte in a sample, and provides a reaction site.

An electrode system comprises a working electrode and a counter electrode, and by applying voltage to perform an oxidation-reduction reaction, the electrode system captures electrons that are generated by the chemical reaction occurring in the reaction layer, where the electrons are electric signals of a current from an electron carrier to the electrode.

A biosensor is used in a combination with a measurement apparatus having various functions such as providing a certain voltage in a predetermined period, measuring electric signals transferred from the biosensor, and converting the electric signals into a concentration of the analyte. Such a system is called a biosensor system.

Among various methods to apply voltage to an electrode system, a method to apply voltage like a rectangular wave with respect to time is called a potential step method. In a typical biosensor system, sample feeding to the biosensor is detected and subsequently, an open circuit or a voltage with substantially no current flow is provided to promote a chemical reaction. After a predetermined period of time, a fixed voltage is applied to deliver electrons between the electron carrier and the electrode, i.e., to perform an oxidation-reduction reaction. A state where the biosensor is provided with a voltage to perform a desired oxidation-reduction reaction is called an excitation state. In general, a current value at an arbitrarily-predetermined point of time during the excitation state is measured, and the current value is converted into a concentration of the analyte, using a calibration curve and a calibration formula that are produced previously.

Methods in which plural excitations and plural current measurements are performed are disclosed, for example, in JP-2651278, JP-A-8-304340, and JP-A-10-10130.

JP-2651278 provides a method to determine whether a current flowing in a reaction site changes in accordance with a relationship with a certain Cottrell current.

JP-A-8-304340 suggests reduction of measurement errors caused by a reduction type intermediate product that is generated during a storage of the sensor.

JP-A-10-10130 provides a method for discriminating a whole blood sample and an aqueous solution as a control in a biosensor system.

Measurement results obtainable by using the biosensor can include errors due to various factors. One of the factors causing such errors is a sample physical property.

For example, when the sample is whole blood and the analyte is glucose in the blood, the hematocrit value (Hct) as a volume ratio of erythrocyte to the whole blood is found to cause errors in the measurement result, and differences between individuals are great. The reason appears to be a rising viscosity of the sample.

Concentrations of neutral fat and protein in the blood also affect the measurement result. In a measurement of an analyte in a blood, sample physical properties, such as blood cells, lipid and protein, will cause measurement errors.

Generally in a conventional method to avoid any influences by such errors, the composition of a chemical reaction layer or of an electrode system in a biosensor is improved. For example, JP-A-62-64940 discloses a biosensor in which an enzyme to detoxify a measurement-interfering substance is immobilized on an enzyme-immobilizing membrane. JP-A-61-3048 discloses a biosensor comprising not only a biocatalytic electrode but an electrode to detect the quantity of measurement-interfering substances. JP-A-60-211350 discloses a biosensor comprising two electrode systems including an electrode system containing an enzyme and a pigment and also an electrode system provided with a porous material containing a pigment only. However, these biosensors with complicated structures require complicated manufacturing processes, and the manufacturing cost is also raised.

Sensor sensitivity can be another factor causing measurement errors. In many cases, sensor sensitivity varies from one manufacturing lot of biosensors to another. Manufactures make sensor sensitivity correction tips for the respective lots, and ship the tips with their biosensors.

When a lot for a biosensor is changed, a user should correct sensitivity by using a correction tip corresponding to the changed lot before he performs an ordinary measurement (JP-A-4-357452).

However, such an operation will impose extra work on the user. Moreover, since the range corrected with such a correction tip is determined based on the sensitivity during manufacture of the sensor, changes of the sensor sensitivity over time, which occur after shipping, will not be corrected.

Since an electrochemical measurement includes a chemical reaction, it is affected also by an environmental temperature and a sample temperature. Namely, an environmental temperature and sample temperature also can be factors of measurement errors. JP-2748196 provides a method of correcting nonlinear temperature dependency of a chemical sensor.

Therefore, the purpose of the present invention is to provide an electrochemical measurement method that can decrease work for users and manufacturers without requiring any complicated structure or process of manufacturing a biosensor and a measurement apparatus. Such a method can provide highly accurate results by correcting errors of concentration of an analyte in a sample.

DISCLOSURE OF THE INVENTION

To achieve the purpose, the present invention provides an electrochemical measurement to measure a concentration of an analyte in a sample by using a biosensor having an electrode system and a chemical reaction layer. The measurement comprises calculation to obtain as parameters a current value obtained as a result of application of a fixed voltage to the sensor after feeding the sample and the ratio of the current value, and calculation of the concentration of the analyte by using a statistical technique. The parameters are set adequately for each error factor affecting the measurement results, and error factors can be corrected directly by selecting parameters that will be affected greatly by the sample physical properties, or by selecting current values that will be affected greatly by the sensor sensitivity.

For the above-mentioned parameters, for example, the following parameters P1 and P2 are preferably used, and the parameters are obtained by applying a predetermined voltage twice to a biosensor after feeding a sample in order to promote an electrochemical reaction.

P1: a ratio (If/Ib), where (If) is the value of maximum current or a current occurring after the maximum in a first excitation, and (Ib) is the value of current (Ib) read at any point in a second excitation P2: a current value (Ib) read at any point in the second excitation With a statistical technique using these two parameters, errors caused by sample physical properties and sensor sensitivity can be corrected with high accuracy. Therefore, the present invention provides measurement with high reliability without requiring any complicated structures or methods of manufacturing sensors, or imposing extra work on users.

In addition to the above-mentioned parameters P1 and P2, the following parameters P3 and P4 also can be used.

P3: a value $(I/\Delta I(\gamma))$ obtained by normalizing a derivative value or a differential value of a current at any point in a second excitation, with a current value at the same point.

Here, "normalization" means adaptation of a ratio of either the derivative value or the differential value to a current value at the same point of time in order to make the derivative value or the differential value a parameter not dependent on the concentration of the analyte. When a ratio of the differential value to a current value is adapted, the current value can be read at any point between two points having a finite difference.

P4: a ratio $(Ib(\alpha)/Ib(\beta))$ of an initial current value $(Ib(\alpha))$ to a terminal current value $(Ib(\beta))$ in a second excitation The inventors consider that these parameters are indices as shown below. However, as it still remains in the realm of speculation, one parameter will not always correspond to one index.

P1: mainly, a current value affected greatly by sample physical properties

P2: mainly, a current value to indicate a concentration of an analyte in a sample P3: mainly, a current value indicating diffusion of a compound and a mixture of a sample and a reactant inside a sensor at a chemical reaction part P4: mainly, a current value affected greatly by the electrode sensitivity of a sensor In the present invention, the current value Ib at any point in the second excitation, which is used for calculating the parameters P1 and P2, is preferably the terminal current value $(Ib(\beta))$ in the second excitation.

When a value of at least either the parameter P3 or P4 is out of the expectation range, the value is preferably substituted by a boundary value of a closest expectation range. This correction will be regarded as an "off-value correction". An expectation range in the present invention is a parameter range that is expected from the concentration of an analyte.

It is preferable in the present invention that correction formulas including a plurality of statistical techniques corresponding to an environmental temperature or a sample temperature are prepared and an optimum correction formula is selected therefrom in order to perform an adequate correction corresponding to either the environmental temperature or the sample temperature. The reason is that the current value obtained by applying voltage to the sensor to make an excitation state varies considerably by the environmental temperature or the sample temperature, and the parameters also vary.

Also, when the environmental temperature or the sample temperature is within the boundary region for a temperature used in the correction, it is preferable to select both the correction methods adjacent to the boundary in order to calculate the respective correction ranges, so that a concentration of the analyte in the sample is calculated based on a value obtainable by adding either an average value or a weighted average value to a current value to be converted into a concentration. When the environmental temperature or the sample temperature corresponds to the boundary region, measurement accuracy will be improved further by selecting both the correction methods adjacent to the boundary in order to obtain an average value or a weighted average value of the obtained correction value rather than selecting one of the methods.

In the present invention, for example, a discriminant function or a Mahalanobis' distance can be used as a statistical technique.

The following explanation concerns a case to use a discriminant function as a statistical technique.

A discriminant function means a linear expression $Z=f(x_1, x_2, \dots)$ defined by plural parameters $(x_1, x_2, \dots)$ in order to discriminate to which of two previously-produced groups (e.g., G1 and G2) the measurement data belong.

Z value code is used to discriminate to which of the groups the data belong. For example, a function to discriminate the level of Hct of a blood sample is defined by using a low Hct group $G_1$ and a high Hct group $G_2$ as populations.

It is preferable to obtain a measurement result by preparing plural discriminant functions in accordance with a concentration of an analyte in a sample, selecting an adequate discriminant function from the discriminant functions using Ib of the parameter P2 as an index, calculating a discriminant score Z value from the selected discriminant function, and by correcting errors with the Z value.

When plural discriminant functions are selected by the indices, it is preferable that Z value is calculated from each of the discriminant functions, and a correction range corresponding to the Z value is calculated, so that the measurement result is obtained from either an average value or a weighted average value of the correction range. As mentioned above, the measurement accuracy will be improved by using an average value or a weighted average value of the correction range rather than using a correction range of any one of the functions.

In a correction using the discriminant function, the correction can be performed to determine to which population the data belong, by using the Z value code. However, it is preferable that the correction range is calculated based on the discriminant score Z value. For example, the discriminant score Z value can be divided into a range to be corrected and a range not to be corrected (correction range is 0).

The range to be corrected can be divided further into a range to be corrected by a correction range proportional to the discriminant score Z value, and a range to be corrected by a fixed correction range without reference to the discriminant score Z value. This can achieve a correction with higher accuracy when compared to a technique performing correction by a grouping depending on the code of the discriminant score. This correction technique will be regarded as "nonlinear correction method" in this description.

In the measurement of the present invention, similarly, a measurement with high accuracy can be achieved by a selection of Mahalanobis' space and a Mahalanobis' distance D in place of the selection of the above-mentioned discriminant function and calculation of the discriminant score Z value as a statistical technique.

In the present invention, preferably, errors caused by sensor sensitivity are corrected after errors caused by sample physical properties are corrected. Since Ib as the parameter P2 is considered to reflect the concentration of the analyte in the sample, it is preferable that errors caused by the sample physical properties and sensor sensitivity with respect to the Ib are corrected, and subsequently, the concentration of the analyte in the sample is calculated based on a value obtained by multiplying this correction value by a temperature correction coefficient.

Furthermore, a measurement apparatus of the present invention comprises a means to measure either an environmental temperature or a sample temperature, a means to detect sample feeding, a means to apply a certain voltage at a predetermined point of time, a means to measure a current value generated by an electrochemical reaction, and a means to convert the measured value of the current into a concentration of an analyte in a sample, wherein the temperature measuring means, the means for detecting sample feeding, the applying means, the means for measuring current value and the conversion means are controlled to perform the present invention. The control is performed typically with a microcomputer having the programmed procedures.

BEST MODE FOR CARRYING OUT THE INVENTION

Figure 1:
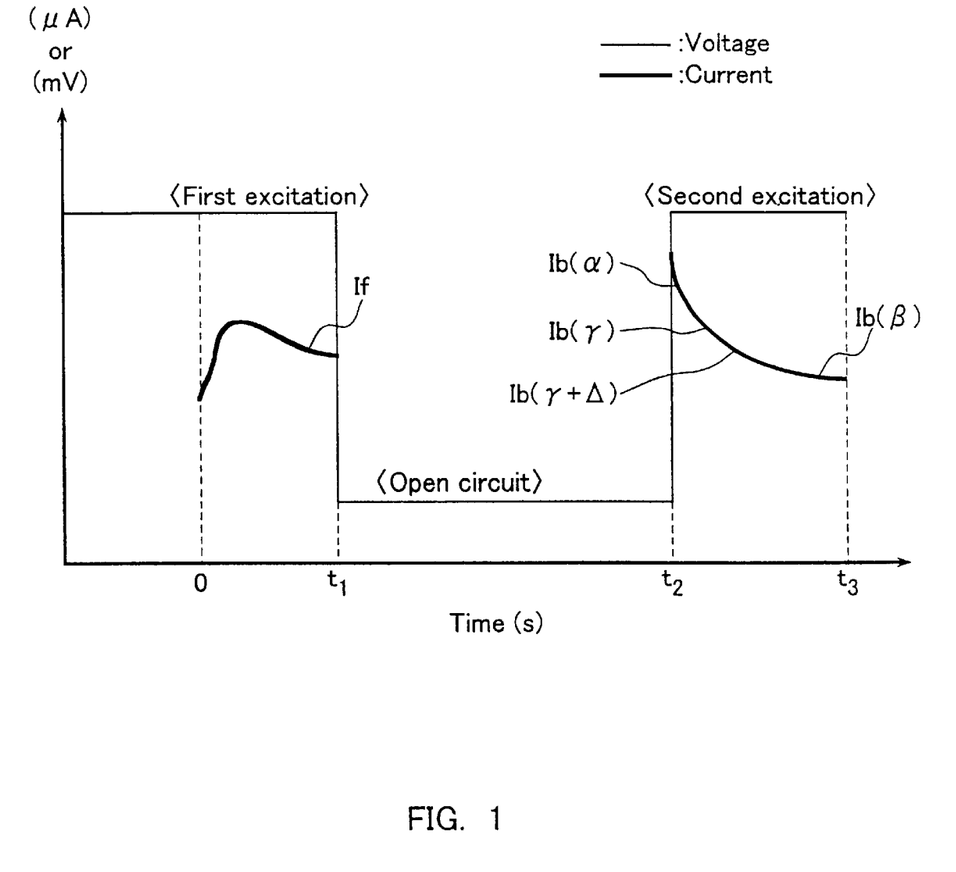
FIG. 1 illustrates a potential step in an embodiment of the present invention.
Figure 2:
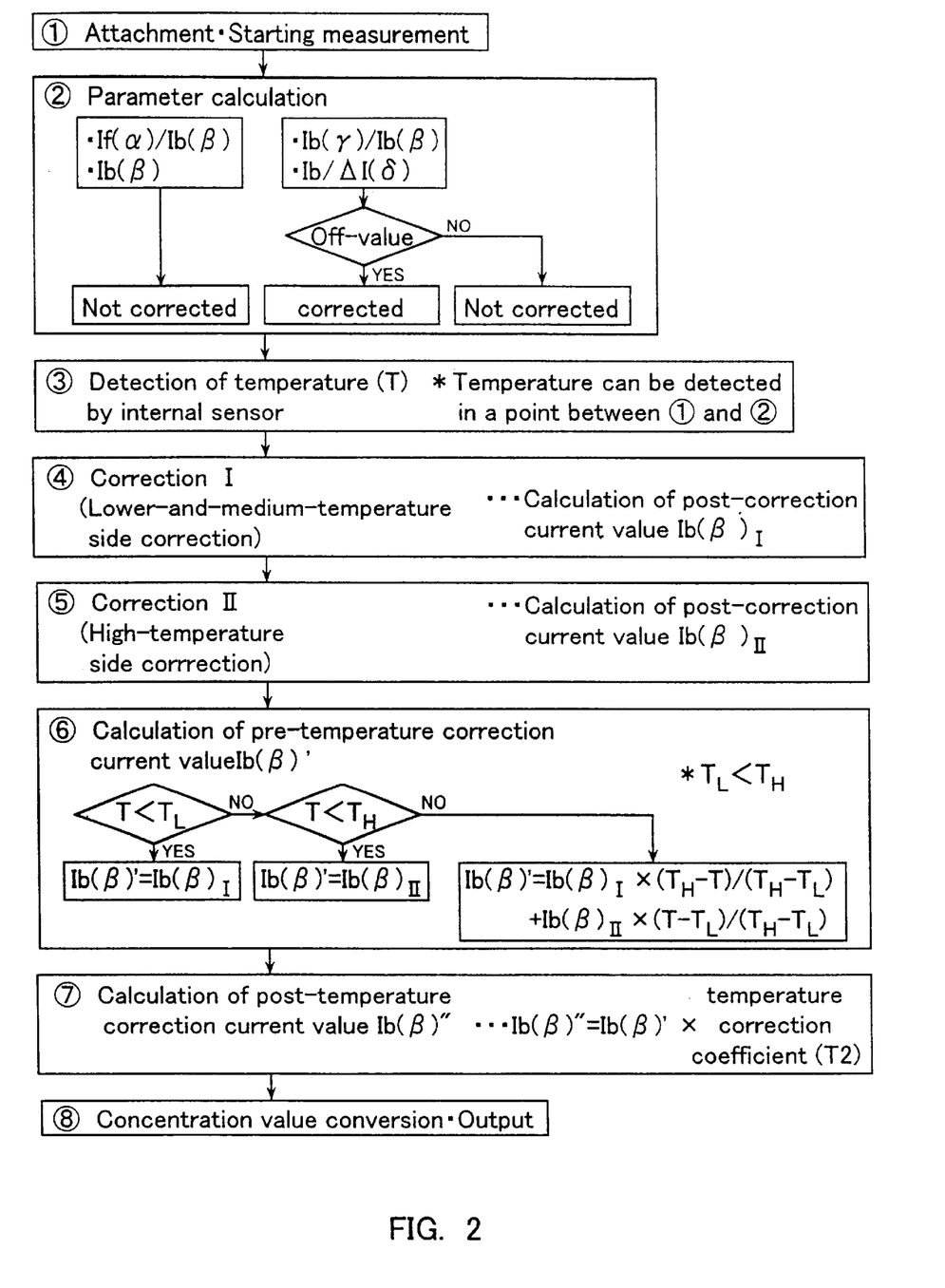
FIG. 2 is a flow chart to illustrate measurement and arithmetic execution in an embodiment of the present invention.
Figure 3:
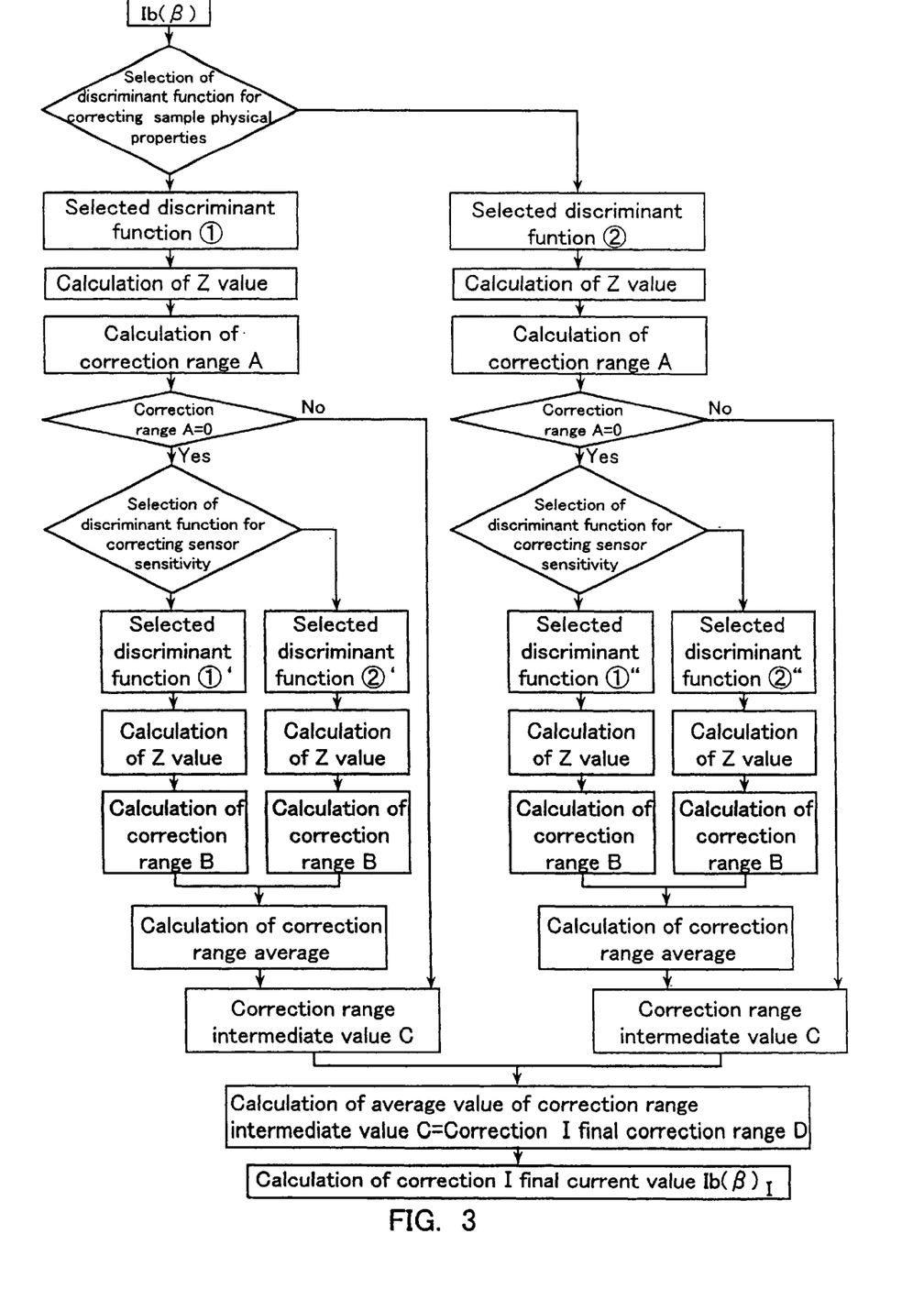
FIG. 3 is a detailed flow chart with respect to correction I in an embodiment of the present invention.

A typical procedure for measurement in the present invention will be explained below with a reference to an example in which the analyte is glucose in blood, and the explanation is based on FIG. 1 illustrating a potential step, FIG. 2 illustrating a measurement-arithmetic execution flow, and FIG. 3 illustrating a correction flow. In this example, errors in the terminal current value in a second excitation, which are caused by sample physical properties and sensor sensitivity, are corrected with a discriminant function, and subsequently, temperature correction is performed and the value is converted into a glucose concentration.

FIG. 1 illustrates a potential step used in the technique of the present invention. A predetermined voltage is applied to an electrode system of a sensor after attaching the sensor to a measurement apparatus. Current begins to flow when a sample is fed to the sensor. A point of time at which a current of at least a certain level is detected is determined as a time of sample feeding, and it is defined as zero second.

A fixed voltage is applied after the detection of the sample feeding, and the application is cancelled after $t_1$ seconds. Therefore, an interval between 0–$t_1$ seconds is a first excitation. Either an open circuit of at most 3 seconds or a process to apply voltage not to cause a substantial oxidation-reduction reaction can be included just after the detection of the sample feeding, because in the present invention, what is important is a value of maximum current or a value of a current thereafter in the first excitation. Voltage in the first excitation is typically in a range from 300 to 900 mV, and $t_1$ is in a range from 3 to 15 seconds in general. As shown in the figure, the current value in the first excitation initially is raised and then lowered after having its maximum value.

After the first excitation, either an open circuit or a voltage not to cause a substantial oxidation-reduction reaction is provided in the interval of $t_1$–$t_2$ seconds. During the interval, glucose, GOD and an electron carrier (e.g., potassium ferricyanide) react in a chemical reaction layer of the biosensor. The interval of $t_1$ to $t_2$ is 3 to 60 seconds in general. During $t_2$–$t_3$ seconds, a voltage to cause a desired oxidation-reduction reaction is applied again to the electrode in order to perform a second excitation. As a result, electrons are delivered between the electron carrier and the electrode, and a current is observed. A voltage in the second excitation is typically 300 to 900 mV, and the time is typically 2 to 10 seconds. The following is a series of the above-mentioned reactions.

The above-described four parameters are calculated using a current value measured in the potential step. First, a current value (If($\alpha$)) of the maximum or a current thereafter in the first excitation and a current value (Ib($\beta$)) in the second excitation are measured to calculate P1 (If($\alpha$)/Ib($\beta$)) and P2 (Ib($\beta$)). The If($\alpha$) is obtained typically by measuring a current value within 15 seconds after the maximum value is observed. The Ib($\beta$) preferably is obtained from a terminal current value 2–10 seconds after the start of the second excitation ($t_2$), and more preferably, it is obtained from the current value at the end point ($t_3$).

P3 (I/$\Delta$I), which is a value obtained by normalizing either a derivative value or a differential value of a current at any point in the second excitation by the above-mentioned current value, is calculated from measured values comprising a current value (Ib($\gamma$)) at a point ($\gamma$) in the second excitation and also a current value (Ib($\gamma$+$\Delta$)) at a point ($\gamma$+$\Delta$) that is positioned slightly later than the point ($\gamma$) in FIG. 1. The point ($\gamma$) to calculate P3 is preferably in a range of 0.1 to 1 seconds from the point of starting the second excitation ($t_2$), while $\Delta$ is preferably in a range of 0.1 to 1 seconds at a slightly later point ($\gamma$+$\Delta$).

An off-value correction is performed for P3 and P4. More specifically, when the parameter value is out of an expectation range estimated from Ib(β), the parameter value is substituted by a boundary value in an expectation range closest to the parameter value and is used for subsequent calculations. P1 and P2 are used for subsequent calculations without such an off-value correction.

On the other hand, an environmental temperature or a sample temperature is measured with an internal thermometer in the measurement apparatus. The temperature is used in the following step to select a discriminant function or to correct a calculation value by correcting errors caused by sample physical properties and sensor sensitivity. The environmental temperature or the sample temperature can be measured either before or after the calculation of the parameters. Of course, it can be measured at the same time of the calculation.

A population is produced and used to define a discriminant function as a standard to distinguish sample properties and sensor sensitivity. In a measurement to produce such a population, it is essential to set conditions of a blood sample, a sensor, and a temperature. It is preferable to set as many conditions as possible for every type of sample and concentration of the analyte. At least two types of groups, e.g., a high value and a low value are set with respect to the sample physical properties. Specifically, measurement data based on a high Hct and a low Hct will be taken when the condition is Hct.

At least 10 lots of sensors are selected so that the manufacture season (elapsed time after manufacture), the manufacture line, sensor sensitivity or the like correspond to a general state of use as much as possible. As many temperature settings as is practical are preferred, and at least two types of settings are required with a boundary of 30 to 35° C., since reactivity of If/Ib used as the parameter with regard to the concentration of the analyte is shaped like a quadratic function having a downward convex curve if the temperature is equal to or lower than the above-mentioned boundary, while the reactivity will be shaped like a substantially straight line if the temperature is equal to or higher than the boundary.

The population is produced by combining the sample and the sensor, which are measured under the respective temperature conditions. Namely, a correction method to deal with errors caused by the sample properties and the sensor sensitivity is prepared under the set conditional temperature. In a correction method explained later in this description, two types of corrections, that is, a lower-and-medium-temperature side correction and a high-temperature side correction are included, in which the boundary is 30 to 35° C.

First, the terminal current value Ib(β) in the second excitation is corrected in the lower-and-medium-temperature side correction. As shown in FIG. 3, this correction includes a correction of errors caused by the sample properties and a correction of errors caused by the sensor sensitivity, which are performed in this order.

Discriminant functions for correcting sample physical properties are prepared for the respective ranges of the analytes' concentrations. The discriminant functions for correcting sample physical properties are produced as discriminant functions to use the parameters for discriminating to which of two populations a certain measurement data belongs, where the populations are classified depending on the heights of Hct. Preferably in this case, data including a parameter considered as an off-value is excluded from the populations, since the populations as standards are preferred to be uniform.

The concentration range of the analytes can be set experientially.

The discriminant function(s) for correcting sample physical properties can be selected according to an index of a value multiplied by Ib(β); it/they can be selected according to an index of a value obtained from a temperature correction coefficient (T1) multiplied by Ib(β), where the temperature correction coefficient is previously calculated from an environmental temperature or a sample temperature measured with a thermometer.

The following is an explanation about a case where a single discriminant function for correcting sample physical properties is selected. First, a parameter calculated in the above-mentioned manner is substituted for the discriminant function for correcting sample physical properties so that a discriminant score Z value is calculated. It is possible to determine to which population the data belongs to, based on this Z value code. Or the Ib(β) can be corrected by determining a correction range from the relation between Ib(β) and the Z value. For example, the Z value is classified into five regions as described below, and the correction range is determined with a nonlinear correction. In the following, "correcting with a fixed range" means correcting with a fixed range determined by a measured Ib(β), regardless of the Z value. The fixed range can be determined experientially by taking the types of the analytes or some other factors into consideration.

A linear correction means to determine a correction range from a proportional relation with the Z value with an upper limit of the above-mentioned fixed range.

Thus determined correction range is regarded as a correction range A. The five regions in the example can be determined experientially taking the types of the analytes and some other factors into consideration.

(1) When the Z value is positioned toward the extreme plus side, it is corrected toward the minus side with a fixed range.

(2) When the Z value is positioned toward the plus side, it is linear-corrected toward the minus side.

(3) When the Z value is positioned in the vicinity of zero, no correction is performed.

(4) When the Z value is positioned toward the minus side, it is linear-corrected toward the plus side.

(5) When the Z value is positioned toward the extreme minus side, it is corrected toward the plus side with a fixed range.

When errors caused by sample physical properties is not corrected (correction range A=0), errors caused by sensor sensitivity are corrected. Discriminant functions for correcting sensor sensitivity also are prepared for the respective concentration ranges of analyte. The discriminant functions for correcting sensor sensitivity are selected with an index of a value obtained by multiplying by Ib(β). When a single discriminant function for correcting sensor sensitivity is selected, a discriminant score Z value is calculated from the parameter and the discriminant function, and a correction range corresponding thereto is calculated. The discriminant function for correcting sensor sensitivity is produced by using the parameter, as a discriminant function to discriminate populations classified based on differences in the electrode sensitivity or the like. When plural discriminant functions for correcting sensor sensitivity are selected, discriminant score Z values and correction ranges corresponding to the Z values are calculated from the respective discriminant functions for correcting sensor sensitivity, and the average value of the correction ranges is determined to be a correction range B.

When the above-mentioned discriminant function(s) for correcting sensor sensitivity is/are used, a correction range intermediate value C is determined in the following manner.

(1) When correction range A≠0, correction range intermediate value C=correction range A
(2) When correction range A=0, correction range intermediate value C=correction range B When plural discriminant functions for correcting sample physical properties are selected, a correction range intermediate value C is calculated in the above-mentioned manner from the respective discriminant functions for correcting sample physical properties, and the average value or a weighted average value is determined as a final correction range D. When a single discriminant function for correcting sample physical properties is selected, the correction range intermediate value C is the final correction range D. A value obtained by adding the final correction range D to the terminal current value (Ib(β)) in the second excitation is the final current value Ib(β)<lower-middle> in the lower-and-middle-temperature side correction.

In a high-temperature side correction, procedures such as data-taking, production of populations and discriminant functions and calculation of correction range are performed similar to the lower-and-middle-temperature side correction, so that a high-temperature side final current value Ib(β)<high> is calculated.

From the temperatures measured with a thermometer, a pre-temperature correction current value Ib(β)' is obtained. For example, Ib(β)'=Ib(β)<lower-middle> at a temperature from 10 to 30° C., and Ib(β)'=Ib(β)<high> at a temperature from 35 to 40° C. The temperature range from 30 to 35° C. is determined as a boundary region, and either the average value or the weight average value of Ib(β)<lower-middle> and Ib(β)<high> is determined as Ib(β)'. The boundary region can be selected experientially by taking the types of the analytes and some other factors into consideration.

The Ib(β)' is multiplied by a temperature correction coefficient (T1) that is calculated previously from an environmental temperature or a sample temperature. The thus obtained value is determined as a post-correction final current value Ib(β)" of Ib(β). And the Ib(β)" is converted into a glucose concentration, using a calibration curve or a calibration formula that is produced previously.

In the respective sections to select discriminant functions for correction as shown in FIG. 3, only ①(①' or ①" for a discriminant function for correcting sensor sensitivity) is selected if a single type should be selected. The correction ranges are calculated respectively from ① and ② (①' and ②', or ①" and ②" for discriminant functions for correcting sensor sensitivity) if two types are selected, and the average values are determined as the correction range intermediate value and the final correction range.

The present invention will be explained in detail with respect to specific embodiments.

A glucose sensor system to quantify a glucose concentration in a blood sample will be taken below as an example of a biosensor system.

A glucose sensor used in the glucose sensor system is configured as follows. On an insulating substrate comprising polyethylene terephthalate (PET), a carbon electrode system and an electrical insulating layer are formed by screen printing, and the carbon electrode system comprises a silver lead, a working electrode and a counter electrode. The electrical insulating layer has a predetermined area in which the working electrode and the counter electrode are exposed, and partially covers the silver lead. On the thus formed electrode system, a layer of carboxymethylcellulose (CMC) as a hydrophilic polymer and further, an (enzyme+mediator+CMC) layer are formed. The (enzyme+mediator+CMC) layer comprises glucose oxidase (GOD) as an enzyme, potassium ferricyanide as a mediator (electron carrier), and a CMC. The combination of the CMC layer and the (enzyme+mediator+CMC) layer is regarded as a chemical reaction layer. An insert comprising a cover and a spacer further is formed, so that a fixed amount (about 3 μL) of a blood sample contacting with the insert is fed by a capillary phenomenon to the chemical reaction layer and to the electrode system. For the measurement apparatus, a commonly-used potentiostat 100B/W (supplied by BAS) was used. While a typical biosensor system uses a combination of a single test cell and an exclusive apparatus, a generalized apparatus is used in the present embodiments. However, the embodiments can be performed easily even if a simple apparatus of a conventional technique is used. The measurement in the embodiments was performed in an environmental test lab, but the embodiments can be performed also by using a simple apparatus containing a temperature sensor.

The potential steps were provided in the following manner.

A glucose sensor was attached to an apparatus, and a voltage of 500 mV was applied to the glucose sensor before sample feeding and for 7 seconds after the detection of sample feeding. After an open circuit of 18 seconds, a voltage of 500 mV was applied again for 5 seconds. The voltage was applied each time for the following purposes. The application before the sample feeding is to detect a current generated electrochemically by the sample feeding. Sample feeding is detected as a current of at least a certain level, and thus, t=0 will be defined. The 7-second application after the sample feeding is for the first excitation, and the main purpose is a detection of difference in the current profile caused by the difference in the sample physical properties. The open circuit of 18 seconds is to promote the chemical reaction and to store $Fe(CN)_6^{4-}$ as a matrix for an electrochemical reaction. The subsequent 5-second application of voltage is for the second excitation, and the main purpose is to convert the $Fe(CN)_6^{4-}$ to $Fe(CN)_6^{3-}$ electrochemically, and to detect a difference in the current profile caused by the difference in the sensor sensitivity and the concentration of the analyte's concentration.

(First Embodiment)

First, errors caused by Hct were corrected, since sample physical properties are the most influential factor to cause errors in a measurement result.

The current was measured at every 0.1 seconds just after the detection of the sample feeding and also after the re-application, and current values at the following three points were used for calculation: the peak value $I_p$ that was measured just after the detection of the sample feeding; I(0.5) that was measured 0.5 seconds after the re-application of current; and I(5) that was measured 5 seconds after the re-application of current. The $I_p$ was calculated in the following manner. Namely, $I_p$ was I(t) at the moment of I(t)>I(t+0.1) in a current just after the detection of the sample feeding. The respective current values were measured for the following purposes. The $I_p$ was measured to detect a difference in the current profile caused by a difference in the sample physical properties such as a blood viscosity. The I(0.5) was measured to see the ratio to $I_p$, so that the glucose concentration factor of $I_p$ would be reduced. The I(5) was measured to obtain a current value that depends on the glucose concentration and that can be used for a glucose concentration conversion.

I(0.5)/$I_p$ was obtained for an index to indicate the blood viscosity, and it was determined as $\alpha_1$. In this embodiment, the following experiment was performed indicating erythrocyte amount with hematocrit, since erythrocyte is a blood cell in a blood sample and it can be adjusted easily.

A relation between $\alpha_1$ and I(5) is shown below, and the relation distinguishes a specimen of 30% hematocrit and a specimen of 60% hematocrit regardless of the glucose concentration in the blood sample.

$$z = -23.115 \times \alpha_1 + 1.254 \times I(5) + 41.580$$

The level of hematocrit in the blood sample is reflected by the value of z. When z is positively large, the hematocrit in the blood sample is considered to be small.

A current value I'(5) after the correction of the sample physical properties was calculated by the following expression from the relation between $\alpha_1$ and I(5).

$$I'(5) = \text{slope} \times (-z) + I(5)$$

In this equation, slope=0.0238×I(5)−0.0338.

The thus calculated current value I'(5) with a corrected blood viscosity will be converted into a glucose concentration value by using a certain calibration curve table.

The following data were obtained using a blood sample (glucose viscosity: 536 mg/dL, hematocrit: 30%).

$I_p$=10.210 ($\mu$A)

I(0.5)=20.290 ($\mu$A)

I(5)=10.110 ($\mu$A)

Regarding the data, a current value I'(5) with a corrected blood viscosity can be obtained through the following arithmetic executions.

$$\alpha_1 = I(0.5)/I_p = 1.987$$

$$z = -23.115 \times \alpha_1 + 1.254 \times I(5) + 41.58 = 8.328$$

$$\text{slope} = 0.0238 \times I(5) - 0.0338 = 0.207$$

$$I'(5) = \text{slope} \times (-z) + I(5) = 8.387$$

This I'(5) will be converted into a glucose concentration value by using a calibration curve that has been produced.

A blood sample used in this embodiment was prepared in the following manner. Blood samples collected from four persons with the identical blood type were mixed to prepare blood samples having hematocrit of 30%, 45% and 60%, respectively. An aqueous solution of glucose was added to these blood samples in order to adjust the glucose concentrations to 83 mg/dL, 307 mg/dL, and 536 mg/dL. Measurement was performed using these 9 types of blood samples, where the measurement number n was determined to be 15.

As explained later in detail, errors caused by hematocrit with regard to blood samples were corrected successfully in this embodiment.

A coefficient of variation (C.V.(%)) is obtained by a calculation based on a group of measurement data for blood samples having different hematocrits for the respective glucose concentrations. The following Table 1 shows the coefficient of variation to compare the values before and after the correction of the sample physical properties.

TABLE 1

| Glucose concentration | Pre-correction | Post-correction |
|---|---|---|
| 83 mg/dL | 5.40% | 3.92% |
| 307 mg/dL | 10.69% | 5.67% |
| 536 mg/dL | 16.52% | 8.56% |

The hematocrit differs depending on individuals. When the standard value is 45% in the present invention, the divergence (%) of the hematocrit 45% specimens from the measured values for the respective glucose concentrations are as shown in Tables 2 and 3. Here, divergence of the post-correction data means a divergence from a corrected average value of hematocrit 45%. Table 2 shows the divergences (%) from measured average values with respect to the cases of hematocrit 30% and of hematocrit 45%.

TABLE 2

| Glucose concentration | Pre-correction | Post-correction |
|---|---|---|
| 83 mg/dL | 4.27% | −0.15% |
| 307 mg/dL | 14.43% | 1.50% |
| 536 mg/dL | 15.69% | −1.92% |

It is clear that errors caused by the physical properties of the blood samples were improved as a result of the correction.

Table 3 shows divergence (%) of measured average values for hematocrit 60% from those for hematocrit 45%.

TABLE 3

| Glucose concentration | Pre-correction | Post-correction |
|---|---|---|
| 83 mg/dL | −4.31% | −1.77% |
| 307 mg/dL | −10.85% | −4.10% |
| 536 mg/dL | −22.21% | −9.12% |

It is clear that errors caused by the physical properties of the blood samples were improved as a result of the correction.

(Second Embodiment)

In this embodiment, a correction of errors caused by an influence of Hct as sample physical properties and a correction of errors caused by sensor sensitivity are performed simultaneously in a series of arithmetic executions.

The current was measured for every 0.1 seconds after the detection of sample feeding, and the following five points were used for the executions: a value If(7) that was measured 7 seconds after the first excitation, a value Ib(0.3) that was measured 0.3 seconds after the second excitation, a value Ib(0.5) that was measured 0.5 seconds after the second excitation, a value Ib(1) that was measured 1 second after the second excitation, and a value Ib(5) that was measured 5 seconds after the second excitation.

The following four parameters were used for the operation:

P1: If(7)/Ib(5)

P2: Ib(5)

P3: I/$\Delta$I(0.5)=Ib(0.5)/{Ib(0.5)−Ib(1)}

P4: Ib(0.3)/Ib(5).

Regarding I/$\Delta$I(0.5) and Ib(0.5)/Ib(5), an off-value correction was performed for the data deviating from a range expected from Ib(5) that is considered as an index for a glucose concentration. Specifically, when the parameter value was higher than the upper limit of the range expected from Ib(5), the upper limit was adapted as the parameter. When the value was lower than the lower limit of the range expected from Ib(5), the lower limit was adapted as the parameter. A range expected from Ib(5) was adapted as a median, and the parameter range was set as the median±2SD from the data derived from a population. For example, when the range of I/$\Delta$I(0.5) expected from the measured Ib(5) was 3.68 and the standard deviation of the parameter was 0.39, a range expected from the Ib(5) was from 2.90 to 4.46, and if the actually obtained I/$\Delta$I(0.5) was 4.50, it was considered as I/$\Delta$I(0.5)=4.46.

Data for making populations for discriminant analysis were obtained at environmental temperatures of 25° C. and 32° C. The blood samples were prepared by mixing blood collected from plural subjects and by adjusting the glucose concentrations to be 30, 60, 75, 100, 150, 200, 250, 300, 400, and 500 mg/dL, and Hct to be 25, 45, and 65%. A glucose sensor manufactured within a year and a half was used, and 10 to 14 lots were selected for every sample so that the lots are selected at random regardless of the manufacture season, manufacture line, and sensor sensitivity. In this embodiment, the following two populations were prepared for every environmental temperature: (1) a population for a Hct correction as a correction of sample physical properties, and (2) a population for correcting sensor sensitivity. Regarding (1), a group of integrated data of three types of Hct specimens with the respective glucose concentrations were classified evenly into five groups depending on the value of Ib(5), and a group ($H_1$) with the largest Ib(5) and a group ($L_1$) with the smallest Ib(5) were adapted as populations. Populations were prepared in this manner without simply taking groups with Hct 25% and with Hct 65%, since correction of the sensor sensitivity was performed preferably as well as the correction of Hct. Regarding (2), a group of data specimens with Hct 45% for the respective glucose concentrations were classified evenly into five groups depending on the value of Ib(5), and a group ($H_2$) with the largest Ib(5) and a group ($L_2$) with the smallest Ib(5) were adapted as populations. Here only the data group with Hct 45% was adapted to improve accuracy in correcting sensor sensitivity, since 45% was considered as a standard Hct value.

A discriminant function is produced as a function to discriminate the populations that have been obtained using parameters for the respective measurement temperatures. Specifically, a discriminant function for Hct correction discriminates between $H_1$ and $L_1$, and a discriminant function for correcting sensor sensitivity discriminates between $H_2$ and $L_2$. In the following, correction I is a correction method using an discriminant function obtained from a measurement data at 25° C., while correction II is a correction method using a discriminant function obtained from a measurement data at 32° C. The correction I indicates a correction under a condition of a lower or room temperature, while the correction II indicates a correction under a high temperature condition. The main reason for classifying the correction method into two categories depending on the temperature is that If(7)/Ib(5) is considerably temperature dependent.

Four types of discriminant functions for Hct correction with regard to the correction I were produced: functions for 30–75 mg/dL, 75–150 mg/dL, 150–300 mg/dL, and 300–500 mg/dL. In a case of 75–150 mg/dL, a discriminant function to discriminate two populations of $H_1$ and $L_1$ for 75 mg/dL and 150 mg/dL was obtained. In this case, the discriminant function was produced so that the discriminant score Z value of a data having high values due to the influence of Hct (i.e., a data of high Hct specimens) would be plus. In producing the populations, data including parameters regarded as abnormal values as a result of a null hypothesis test of Grubs-Smirnor were eliminated, since the populations were preferably as uniform as possible.

The discriminant function for Hct correction was produced by selecting a value as an index obtained by multiplying a temperature correction coefficient (T1) by Ib(5), where the temperature correction coefficient was calculated previously from the environmental temperature, and the selection numbers were 1–2. T1 was determined as 1 at 25° C., a temperature that is considered as a standard. A case where plural discriminant functions were selected will be described later. When a single discriminant function for Hct correction was selected, the parameter was substituted for the discriminant function, and a discriminant score Z value and a correction range A corresponding thereto were calculated. The correction range A was determined with a nonlinear correction method. Namely, when $Z_A < Z_B < Z_C < Z_D$ ($Z_A$, $Z_B$, $Z_C$, $Z_D$ are constants experientially determined for every discriminant function) and when a current value Ib(5) and a discriminant score Z value were obtained, corrections were performed as follows: when $Z < Z_A$, correction was performed with a fixed range toward the plus side regardless of Z value; when $Z_A \leq Z < Z_B$, a linear correction was performed toward the plus side corresponding to the Z value; when $Z_B \leq Z < Z_C$, no correction was performed; when $Z_C \leq Z < Z_D$, a linear correction was performed toward the minus side corresponding to the Z value; and when $Z_D \leq Z$, a correction with a fixed range was performed toward the minus side regardless of the Z value. The correction with a fixed range means correcting with a fixed range determined by a measured Ib(5) for every discriminant function. A linear correction is determining a correction range from a proportional relation with the Z value with an upper limit of the above-mentioned fixed range. For example, if a linear correction is performed toward the minus side when $5 \leq Z < 10$, the correction range is −0.10 for $Z \geq 10$, a correction range for Z=8 is calculated according to the following equation (1).

$$\text{Correction range } A = -0.01 \times (8-5)/(10-5) = -0.06 \quad (1)$$

The term 'correction of a fixed range' means that a correction range will have a fixed value once Ib(5) is determined. The correction range itself varies in accordance with Ib(5). When no Hct correction was performed (correction range A=0), the sensor sensitivity as mentioned above was corrected as described below in order to obtain a correction range B. When Hct correction was performed (correction range A≠0), correction of sensor sensitivity will not be performed.

Seven types of discriminant functions for correcting sensor sensitivity with regard to correction I were prepared: functions for 75–100 mg/dL, 100–150 mg/dL, 150–200 mg/dL, 200–250 mg/dL, 250–300 mg/dL, 300–400 mg/dL and 400–500 mg/dL. In a case of 75–100 mg/dL, a discriminant function to discriminate two populations of $H_2$ and $L_2$ for 75 mg/dL and 100 mg/dL was obtained and the function was determined as a discriminant function for correcting sensor sensitivity for the above-identified concentration ranges. In this case, the discriminant function was produced, so that the discriminant score Z value measured with a highly sensitive sensor would be plus. In producing the populations, data including parameters regarded as extremely high/low as a result of a null hypothesis test of Grubbs-Smirnov were eliminated, since the populations were preferably as uniform as possible similar to the above-mentioned case of producing a discriminant function for Hct correction.

The discriminant function for correcting sensor sensitivity was selected with Ib(5) as an index, and the selection numbers were 1–2. When a single discriminant function was selected, the parameter value was substituted for the discriminant function, and a discriminant score Z value and a correction range corresponding thereto were calculated. The correction range was regarded as a correction range B. The correction range was determined with a nonlinear correction method similar to the case of Hct correction. When plural discriminant functions were selected, correction ranges were calculated from the respective discriminant functions, and the average value was regarded as the correction range B.

A correction range intermediate value C was determined as follows when a single discriminant function for Hct correction was selected.

(1) When correction range A≠0, correction range intermediate value C=correction range A
(2) When correction range A=0, correction range intermediate value C=correction range B When two types of discriminant functions for Hct correction were selected, a correction I final correction range D was obtained in a similar way by obtaining an average value or a weighted average value of the correction range intermediate values C obtainable from the respective discriminant functions for Hct correction. When only one type of discriminant function for Hct correction was selected, a correction range intermediate value C thereof was determined as the correction I final correction range D. The correction I final current value $Ib(5)_I$ was a value obtained by adding the final correction range to Ib(5).

Regarding the correction II, the technique of the correction I was adapted to take data, produce populations and discriminant functions, and to calculate correction ranges, so that a Correction II final current value $Ib(5)_{II}$ was obtained.

A pre-temperature correction current value Ib(5)' was determined as follows from a temperature T (° C.) detected with a temperature sensor.

When $T<30$, $Ib(5)'=Ib(5)_I$.

When $30 \leq T \leq 35$, $Ib(5)'=(35-T)/(35-30) \times Ib(5)_I+(T-30)/(35-50) \times Ib(5)_{II}$.

When $T>35$, $Ib(5)'=Ib(5)_{II}$.

For example, Ib(5)' can be obtained from the following equation when T=32° C.:

$$Ib(5)'=3/5 \times Ib(5)_I+2/5 \times Ib(5)_{II}$$

Ib(5)" was obtained by multiplying thus obtained Ib(5)' by a temperature correction coefficient (T2). This Ib(5)" was converted into a glucose concentration value according to a calibration curve table that was produced separately.

For example, the following data were obtained by measuring blood specimens of a glucose concentration of 154 mg/dL and Hct 65% under an environmental temperature of 25° C.

If(7)=2.142($\mu$A)

Ib(0.3)=7.578($\mu$A)

Ib(0.5)=6.312($\mu$A)

Ib(1)=4.932($\mu$A)

Ib(5)=2.142($\mu$A)

The following parameters are obtained from the above-identified data.

If(7)/Ib(5)=0.8069

I/$\Delta$I(0.5)=Ib(0.5)÷{Ib(0.5)−Ib(1)}=4.575

Ib(0.3)/Ib(5)=2.855

Ib(5)=2.654

At this time, expectation ranges of I/$\Delta$I(0.5) and Ib(0.3)/Ib(5) are calculated from the value of Ib(5) respectively to be 3.050–4.496 and 2.817–4.361. Since I/$\Delta$I(0.5) exceeds the upper limit of the expectation range and thus is considered as an off-value, I/$\Delta$I(0.5)=4.496 in the subsequent calculations.

Correction I is performed. A discriminant function for Hct correction is selected with an index of Ib(5)=2.654. When Ib(5) ranges from 2.407 to 3.400, a discriminant function for 75–150 mg/dL and a discriminant function for 150–300 mg/dL are used. The discriminant functions are defined respectively as follows. A discriminant function for 75–150 mg/dL·Hct correction:

$$Z(L)=34.525 \times P1-27.333 \times P2-21.717 \times P3+3.1870 \times P4+141.90.$$

A discriminant function for 150–300 mg/dL·Hct correction:

$$Z(N)=331.25 \times P1-16.739 \times P2-22.331 \times P3+6.7191 \times P4-158.00.$$

In these equations, P1=If(7)/Ib(5), P2=I/$\Delta$I(0.5), P3=Ib(0.3)/Ib(5), and P4=Ib(5).

In this embodiment, Z(L)=−5.753. Since a linear correction is performed toward the plus side when −8≤Z(L)<−4, a correction range $A_L$ is calculated from the following equation:

$$A_L=\{0.1205 \times Ib(5)-0.1049\} \times \{-4-Z\}/\{-4-(-8)\}=0.1024.$$

The sensor sensitivity will not be corrected since $A_L \neq 0$. The value of 0.1024 will be a correction range intermediate value $C_L$.

In this embodiment, Z(N)=−11.887. Since no correction is performed when −15≤Z(N)<5, the sensor sensitivity will be corrected. Since Ib(5)×temperature correction coefficient (T1)=2.654 and this figure is within a range of 2.582–3.316, a discriminant function used for correcting sensor sensitivity is of 150–200 mg/dL. The discriminant function of 150–200 mg/dL is defined as follows. A discriminant function for correcting sensor sensitivity of 150–200 mg/dL:

$$Z(S_3)=43.581 \times P1-25.041 \times P2-25.472 \times P3+2.0536 \times P4+141.86.$$

In this equation, P1=If(7)/Ib(5), P2=I/$\Delta$I(0.5), P3=Ib(0.3)/Ib(5), and P4=Ib(5).

In this example, $Z(S_3)$=−2.827.

Since a linear correction is performed toward the plus side when −6≤$Z(S_3)$<−2, a correction range $B_N$ is calculated from the following equation. This $B_N$ will be a correction range intermediate value $C_N$.

$$B_N=C_N=\{0.0312 \times Ib(5)-0.0121\} \times \{-2-Z(S3)\}/\{-2-(-6)\}=0.0146$$

Since two discriminant functions for Hct correction are selected in this example, a final correction range $D_I$ of the correction I is an average value obtained from the two correction range intermediate values $C_L$ and $C_N$:

$$D_I=(0.1024+0.0146) \div 2=0.0585.$$

Therefore, a post-correction current value $Ib(5)_I$ obtainable by the correction I can be obtained in the following manner.

$$Ib(5)_I=2.654+0.0585 \approx 2.713$$

Since the temperature is 25° C. and the pre-temperature correction current value $Ib(5)'=Ib(5)_I$, calculation procedures for obtaining $Ib(5)_{II}$ will be omitted from the following description. Since the temperature is 25° C., the temperature correction coefficient is 1 and the post-temperature correction current value Ib(5)"=Ib(5)'=2.713. This Ib(5)" value is substituted for a calibration curve produced separately in order to be converted into a glucose concentration. An average value of Ib(5) of a data of a glucose concentration of 154 mg/dL and Hct 45%, i.e., an expectation value of Ib(5) for a glucose of 154 mg/dL was 2.790. A correction according to the present invention decreased divergence from the expectation range (pre-correction value=2.142; post-correction value=2.713).

In this embodiment, errors caused by sample physical properties and sensor sensitivity were decreased. This will be explained below referring to an result of a case where the glucose concentration was 150 mg/dL.

Ten lots×number N (10) of sensors were measured for every Hct specimen. The coefficient of variation (CV)(%) for the entire measurement data varied before and after the correction as described below. The table below shows that errors caused by sensor sensitivity is decreased.

TABLE 7

| Specimen Hct | Pre-correction | Post-correction | Correction effect (Pre-correction−Post-correction) |
|---|---|---|---|
| 25% | 4.7% | 4.3% | Δ0.4% |
| 45% | 4.5% | 4.2% | Δ0.3% |
| 65% | 5.1% | 4.7% | Δ0.4% |

Since the hematocrit differs depending on individuals, the standard value is 45% in the present invention. Divergences (%) of the respective Hct specimen current average values from a Hct 45% specimen current average value are shown in Table 2. It is clear from this table that errors caused by Hct were corrected further.

TABLE 8

| Specimen Hct | Pre-correction | Post-correction | Correction effect (Pre-correction−Post-correction) |
|---|---|---|---|
| 25% | 15.6% | 8.2% | Δ7.4% |
| 65% | −7.2% | −3.8% | Δ3.4% |

As an index to indicate a maximum divergence of an obtained measurement value from a true value or from an expectation value, a total error (TE) is considered. TE is defined as follows.

$$TE(\%)=DEV(\%)+1.65 \times CV(\%)$$

A coefficient 1.65 of a CV term is a value of Z value (a value not as a discriminant score but as a value in a standard normal distribution) composing one-sided probability of 5% of a standard normal distribution, and TE defined in this term is a divergence range from a true value to which 95% of the entire data is considered to be included.

TE in this example is as shown in Table 3.

TABLE 9

| Specimen Hct | Pre-correction | Post-correction | Correction effect (Pre-correction−Post-correction) |
|---|---|---|---|
| 25% | 23.3% | 15.3% | Δ8.0% |
| 45% | 7.4% | 7.0% | Δ0.3% |
| 65% | 15.6% | 11.5% | Δ4.4% |

INDUSTRIAL APPLICABILITY

As mentioned above, according to the measurement method of the present invention, errors with respect to analytes caused by factors such as sample physical properties and sensor sensitivity can be corrected efficiently without modifying compositions of a chemical reaction layer or an electrode system of a sensor, and thus, a reliable measurement value can be obtained.

What is claimed is:

1. An electrochemical measurement method to measure a concentration of an analyte in a sample by using a biosensor, wherein the concentration of the analyte is obtained by providing a sample to the biosensor, applying first and second predetermined voltages to the biosensor to which the sample has been provided, calculating parameters P1 and P2 from current values that are obtained as a result of applying a fixed voltage to the biosensor, and by correcting the errors from these parameters by a statistical technique, where P1: a ratio (If/Ib), where (If) is the value of maximum current or a current occurring after the maximum in a first excitation caused by applying the first predetermined voltage, and (Ib) is the value of current read at any point in a second excitation caused by applying the second predetermined voltage;

P2: a current (Ib) read at any point in the second excitation caused by applying the second predetermined voltage, and determining the analyte concentration using the parameters P1 and P2.

2. The measurement method according to claim 1, wherein the current value Ib at any point in the second excitation used for the parameters P1 and P2 is a terminal value (Ib(β)) in the second excitation current.

3. The measurement method according to claim 1, wherein at least one of parameters P3 and P4 is used together with the parameters P1 and P2, where P3: a value (I/ΔI(δ)) obtained by normalizing a derivative value or a differential value at any point in the second excitation with a current value at the same point; and P4: a ratio (Ib(α)/Ib(β)) of an initial current value (Ib(α)) to a terminal current value (Ib(β)) in a second excitation.

4. The measurement according to claim 3, wherein at least one of the parameters P3 and P4 is substituted with a closest expectation value when the parameter is out of an expectation range.

5. The measurement method according to claim 1, including measuring an environmental temperature or a sample temperature, wherein a correction is performed in accordance with the environmental temperature or the sample temperature by preparing a plurality of correction formulas using a statistical technique corresponding to the environmental temperature or the sample temperature and by selecting an optimum correction formula from the plural correction formulas.

6. The measurement method according to claim 5, wherein the concentration of the analyte in the sample is obtained when the environmental temperature or the sample temperature corresponds to a boundary region of the temperature range used for a correction formula, by selecting both correction formulas adjacent to a boundary, calculating correction ranges from the respective formulas, adding average values or weighted average values to the current value for concentration conversion, and obtaining the concentration depending on an additional value.

7. The measurement method according to claim 1, wherein a discriminant function is selected from the parameters.

8. The measurement according to claim 7, wherein a discriminant score is obtained from the discriminant function and the concentration of the analyte is calculated from a correction range proportional to the discriminant score.

9. The measurement method according to claim 7, wherein a range to calculate the concentration of the analyte depending on a fixed correction range regardless of the discriminant score, and a range to calculate the concentration of the analyte without performing a correction, are set.

10. A measurement apparatus comprising a meter for measuring an environmental temperature or a sample temperature, a detector for detecting sample feeding, a device for applying a certain voltage to a biosensor at a predetermined point of time, a meter for measuring a value of current generated by an electrochemical reaction, and a converter for converting the measured value of the current into a concentration of the analyte in the sample;

including means for measuring the concentration of an analyte, means for feeding a sample, means for applying first and second predetermined voltages to the biosensor after sample feeding, means for calculating parameters P1 and P2 from current values that are obtained as a result of applying a fixed voltage to the biosensor, and means for correcting errors of a measured value using these parameters by a statistical technique, where P1: a ratio (If/Ib), where (If) is the value of maximum current or a current occurring after the maximum in a first excitation caused by applying the first predetermined voltage, and (Ib) is the value of current read at any point in a second excitation caused by applying a second predetermined voltage after the first predetermined voltage;

P2: a current (Ib) read at any point in the second excitation caused by applying the second predetermined voltage.

* * * * *